United States Patent [19]

Adams et al.

[11] Patent Number: 4,986,920

[45] Date of Patent: Jan. 22, 1991

[54] SELECTIVE RECOVERY OF A NITROPHENOLIC BY-PRODUCT FROM NITRATION WASTE WATER BY PRECIPITATION

[75] Inventors: Earl G. Adams, Grand Bay, Ala.; Arthur C. Bayer, Ocean Springs, Miss.; Alan D. Farmer, Biloxi, Miss.; Brenda J. Hook, Gautier, Miss.

[73] Assignee: First Chemical Corporation, Pascagoula, Miss.

[21] Appl. No.: 377,105

[22] Filed: Jul. 10, 1989

[51] Int. Cl.$^5$ ............................................. C02F 1/26
[52] U.S. Cl. .................................... 210/710; 210/909
[58] Field of Search ............... 210/634, 710, 724, 909; 568/757

[56] References Cited

U.S. PATENT DOCUMENTS 4,597,875  7/1986  Carr et al. ...................... 210/724 X

*Primary Examiner*—Frank Spear
*Attorney, Agent, or Firm*—A. W. Breiner

[57] ABSTRACT

A process of selectively recovering a nitrophenolic by-product, namely 2,4-dinitrophenol and picric acid, from nitration waste water in substantially pure form through the control of the solution pH of the nitration waste water and subsequent precipitation is provided. By adjusting the solution pH of the nitration waste water with an acid to a pH in the range of from about 4.0 to 0.5, the solubility of the selected nitrophenolic by-products is affected and the crystal formation of the individual by-products controlled.

6 Claims, No Drawings

SELECTIVE RECOVERY OF A NITROPHENOLIC BY-PRODUCT FROM NITRATION WASTE WATER BY PRECIPITATION

RELATED APPLICATIONS

The present application is related to (1) an earlier filed application entitled "Process For Extracting And Disposing Of Nitrophenolic By-Products", U.S. Ser. No. 07/242,882 filed Sept. 12, 1988 and (2) a concurrently filed application entitled "Selective Recovery Of A Nitrophenolic By-Product From Nitration Waste Water By Extraction" having the same inventors.

FIELD OF INVENTION

The present invention is directed to the selective recovery of nitrophenolic by-products in substantially pure form from nitration waste water. In particular, the invention is directed to the separate recovery of 2,4-dinitrophenol and picric acid from nitration waste water by controlling the solution pH of the waste water utilizing an acid prior to precipitation of the selected by-product.

BACKGROUND OF THE INVENTION

During a nitration process to produce a desired chemical product, such as nitrotoluene or nitrobenzene, nitrophenolic by-products are produced. These nitrophenolic by-products are usually present in the form of a mixture of di- and tri-nitrophenols and/or di- and tri-nitrocresols. The by-products are separated from the desired nitrated product by washing. The by-products are then present in the wash water or waste water stream which must be disposed of in some environmentally safe manner.

Various processes are known in the art for disposing of waste water containing nitrophenolic materials. One process which has been used for disposing of nitration waste water is to collect the waste water from the nitration washers in a lagoon and adjust the pH of the waste water to approximately 1.5 to cause substantially all of the phenolic compounds present in the waste water to indiscriminately precipitate. The precipitate is not recovered for reuse. Due to environmental concerns and the increasing number of chemical by-products, however, lagooning is no longer considered a viable environmentally safe method of disposal.

Currently contemplated methods of waste water disposal require removal of the nitrophenolic by-products before the waste water can be disposed of to avoid damage or potential damage to the environment. However, the by-products are not recovered in a substantially pure form suitable for commercial sale, but simply separated from the waste water indiscriminately to put the waste water in a suitable form for disposal. The recovered by-products are disposed of separately from the water, such as by incineration. For example, U.S. Pat. No. 4,597,875 discloses the production of dinitrotoluene with the concurrent production of nitrophenolic by-products, i.e. nitrocresols and picric acid. Prior to disposal of the waste water, the by-products are removed from the waste water. The waste water is first contacted with an alkaline material to convert the by-products to water soluble salts. An organic and aqueous phase are generated. The aqueous phase, which contains nitrophenolic materials, is separated out and treated with an acid to convert the salts to a water insoluble material. The water insoluble materials separate into an organic phase containing the converted nitrophenolic materials and an aqueous phase containing water soluble salts. The organic phase, due to its lower water content, can then be incinerated to dispose of the contaminants.

U.S. Pat. No. 655,117 discloses a process for separating an isomeric mixture of meta- and para-cresols. The process of separation is based on the ready solubility of m-cresol-sulphonic acid in sulfuric acid and the substantial insolubility of para-cresol-sulphonic acid in sulfuric acid. The cresol mixture is heated with concentrated sulfuric acid to convert the cresols to their respective sulphonic acid forms. The resulting products are allowed to stand in order to allow the para-cresol-sulphonic acid to crystalize out of the mixture. The crystalized cresol is then removed from the mother liquor by filtration. Thereafter, the sulfuric acid is split off from the cresol by superheated steam in order to obtain the pure para-cresol. The m-cresol remains in the mother liquor.

U.S. Pat. No. 1,025,615 discloses the separation of meta- and para-cresols using sulfuric acid by converting the cresols to sulphonic acids. The '615 patent is similar to the '117 patent noted above, except that the meta-cresol-sulphonic acid is crystalized and recovered in the process disclosed rather than the para-cresol-sulphonic acid which is recovered in the process of the '117 patent.

U.S. Pat. No. 1,473,750 discloses the purification of waste water from coke plants. The waste water contains various substances, including phenol, cresol, hydrocyanic acid, hydrogen sulphide, thiocyanates and calcium salts. The disclosed purification process includes the steps of neutralizing the waste water with sulfuric acid, allowing the neutralized waste water to stand so that the salts formed can precipitate out, decanting the liquid from the precipitate, and contacting the recovered liquid with coke oven gas. The materials in the precipitate are not separated out or selectively recovered.

U.S. Pat. No. 4,491,677 discloses the use of a phenolic compound and a solvent to crystalize a particular cresol from a mixture of cresols obtained from refinery waste streams. The procedure involves contacting the cresol mixture with a phenolic compound and solvent and thereafter allowing the solution to stand and cool so that the desired cresol precipitates.

U.S. Pat. No. 2,275,045 discloses a preparation for phenolic compounds wherein the phenols are initially obtained in the form of a metal salt such as calcium phenate. The phenol is recovered by acidifying the reaction mixture with a strong mineral acid to decompose the calcium phenate so that the phenol can be steamed distilled from the acidified mixture.

U.S. Pat. No. 4,746,443 discloses a process of purification of waste water containing bentazon involving the decomposition of the bentazon. The process includes the adjustment of the waste water pH to a level between 0.2 and 7 utilizing an acid, such as sulfuric acid, followed by the heating of the acidified waste water to at least 60° C. The water is neutralized with an alkaline material prior to discharge.

The art does not disclose affecting the solubility of a nitrophenolic by-product contained in nitration waste water, which is made up of a plurality of nitrophenolic by-products, utilizing an acid to selectively recover the nitrophenolic by-product in substantially pure form by precipitation. Furthermore, the art does not disclose a process of recovering a nitrophenolic by-product from nitration waste water in a form suitable for commercial sale.

The ability to selectively recover a particular nitrophenolic by-product in substantially pure form from nitration waste water utilizing an acid is surprising in that while an acid has been used in the past to precipitate nitrophenolic compounds, the prior art methods require additional purification steps to obtain any particular nitrophenol in a substantially pure form. According to the prior art methods, the acid indiscriminately precipitates all materials. Where additional purification steps have not been used, it was because only an isomeric mixture of nitrocresols was acted upon by an acid rather than a mixture of varying nitrophenolic compounds such as present in nitration waste water. Selective precipitation based on the pH control of a mixture of isomeric and nonisomeric nitrophenolic materials, which does not require additional purification steps, is an important economic and environmental advance.

OBJECTS OF THE INVENTION

A primary object of the present invention is to provide a process for selectively recovering a nitrophenolic by-product in substantially pure form from nitration waste water by affecting the solubility of the nitrophenolic by-product through the control of the waste water pH to effect the selective crystalization of the desired nitrophenolic by-product.

A further primary object of the present invention is to provide a process for the selective recovery of a nitrophenolic by-product from nitration waste water wherein the by-product is recovered in a form suitable for commercial sale.

A further primary object of the present invention is to provide a process for removing a contaminant from nitration waste water so that the water contains fewer or no contaminants and thus is placed in a more favorable condition for an environmentally safe disposal.

GENERAL DESCRIPTION OF THE INVENTION

The present invention provides an economical and efficient process for treating contaminant containing waste water, also known as "red water", resulting from the washing of nitrated products in chemical plants to remove oxidation by-products produced during the nitration process. These by-products, which make up the contaminants in the waste water, are mainly nitrophenolic materials such as di- and tri-nitrophenols and di- and tri-nitrocresols.

The process of the present invention provides for the selective recovery of certain of these nitrophenolic by-products, namely 2,4-dinitrophenol (2,4-DNP) and picric acid, by precipitation wherein the recovered by-product is in substantially pure form, i.e. in a form suitable for commercial sale. "In substantially pure form" is understood to mean that the recovered nitrophenolic material, i.e. 2,4-DNP or picric acid, has at most 5% impurities (on a dry basis).

An example of a nitration process which results in the production of a waste water stream containing the nitrophenolic by-products of dinitrophenol and picric acid, is the nitration of benzene with nitric acid in the presence of sulfuric acid to produce nitrobenzene and the above-described by-products. In the production of mononitrobenzene, the specific nitrophenolic by-products which can result include 2,6-dinitrophenol (2,6-DNP), 2,4-DNP, and picric acid. The 2,6-DNP is produced in a minor or trace amount when an adiabatic nitration process is utilized. This 2,6-DNP will generally be the main impurity in the 2,4-DNP. It is noted that the isothermal or conventional nitration process does not produce picric acid, but does produce about 10% to 20% of the 2,6-DNP isomer and some mononitrated phenols. The adiabatic process produces about 1% to 6% 2,6-DNP. Some isolation of the 2,6-DNP isomer from the 2,4-DNP can occur when a preliminary extraction or precipitation occurs, such as that used to remove cresols. Due to the low concentration of 2,6-DNP in the feed waste water stream of the adiabatic process, less than 500 parts per million (ppm), as compared to the concentration of 2,4-DNP of about 5,000 ppm and picric acid of about 5,000 ppm, the solubility of 2,6-DNP is not greatly exceeded when acidification is performed. The fact that the solubility limit is not exceeded helps to reduce the amount of 2,6-DNP which appears in the 2,4-DNP product. The normal amount of 2,6-DNP present in the 2,4-DNP is from about 1% to 4%.

Following the nitration process, the nitrophenolic by-products are separated from the nitrated products by washing. A base, such as sodium hydroxide, is typically utilized to wash the nitrated product. The nitrated phenols are organic acids which vary in acidity from the acidity of carbonated water to being more acidic than phosphoric acid. These organic acids have a high solubility in nitrated aromatics and a low solubility in water. When a base is reacted with these acids, a salt is formed which is nearly insoluble in hydrocarbon solvents and very soluble in water. By utilizing countercurrent extraction, these salts can be washed from the nitrated product.

A primary factor in selectively recovering a particular substantially pure nitrophenolic by-product from a plurality of nitrophenolic by-products according to the present invention is the control of the nitration waste water's pH. By decreasing the solubility of the nitrophenolic by-product to be recovered, crystal formation of the by-product is encouraged. The waste water pH is controlled through the addition of an acid, more particularly sulfuric acid, to the waste water to increase the solution acidity of the waste water. It has been found that the individual organic solutes sought to be recovered, i.e. 2,4-DNP and picric acid, each have a unique pH range in the waste water at which crystal formation begins due to their individual solubility and other physio-chemical characteristics. The selective precipitation of 2,4-DNP and picric acid from nitration waste water containing these compounds involves first removing the material having the higher pKa, i.e., precipitating 2,4-DNP first. The designation pKa is used in the conventional sense and signifies the value where the acid and salt concentrations are equal. Accordingly, by selectively controlling the pH of the waste water, selectivity in crystal precipitation of a particular nitrophenolic by-product from nitration waste water can be obtained.

More specifically, the process of the present invention is carried out by placing nitration waste water containing nitrophenolic by-products, wherein at least one of the by-products present is 2,4-DNP or picric acid, in a reaction container having any conventional means of agitation. The waste water is agitated while small amounts of sulfuric acid are added to the water solution. The solution pH is monitored during the addition of the sulfuric acid. The acid addition is continued until the solution pH has been adjusted to a desired level suitable for the selective recovery of a particular nitrophenol. The amount of sulfuric acid added will vary depending upon the initial pH of the waste water and the level to which the pH is lowered. The sulfuric acid is preferably added in small quantities to allow for suitable mixing and to better insure an accurate monitoring of the solution pH.

Once the desired pH is reached, the pH level is allowed to stabilize. When 2,4-DNP is to be recovered, the pH will be adjusted to a level in the range of from about 4.0 to 2.0; preferably, the pH is adjusted to from about 2.5 to 3.0, and most preferably the pH is adjusted to 2.5 to obtain the 2,4-DNP in its most pure condition. When the desired nitrophenolic by-product to be recovered is picric acid, the pH will be adjusted to a level in the range of from about 0.5 to 0.7, and preferably to a pH of 0.6 to obtain the highest level of purity and best yields. It is possible that some picric acid may precipitate at a pH of 2.0. However, such precipitation will not be very much since the pKa is 0.38. At a pH cf 0.6, the precipitate recovered will contain better than 60% of picric acid.

As described above, to obtain picric acid in a substantially pure form, most of the 2,4-DNP should first be removed since 2,4-DNP has a higher pKa than picric acid. It is preferred that following the precipitation of the 2,4-DNP, that the waste water be subjected to a solvent extraction to extract any non-recovered 2,4-DNP. A solvent extraction, such as with toluene, reduces the level of 2,4-DNP down to less than about 100 ppm in the waste water. This improves the quality of the picric acid recovered. The pH of the waste water can be lowered to about 2.0 to 2.5 to facilitate the 2,4-DNP extraction. Precipitation alone of the 2,4-DNP leaves approximately from about 500 to 1,000 ppm of 2,4-DNP in the waste water and accordingly, the picric acid quality will be lower. Recovery of the picric acid without the prior extraction, however, still results in picric acid present in a substantially pure form.

During each precipitation step, the particular nitrophenolic compound being recovered crystalizes or precipitates from the solution. The crystals are allowed to settle in the reaction container. The solution, i.e. nitration waste water, is then separated from the formed crystals by siphoning or pouring off of the liquid from the crystals. Preferably, the separation is performed by vacuum filtration. The obtained crystals are then washed with water. The nitrophenolic compound recovered in crystal form is in a substantially pure form suitable for commercial sale.

DESCRIPTION OF PRESENTLY PREFERRED EMBODIMENTS

The process of the present invention is illustrated using the general procedure as set forth above in relation to both non-cresol contaminated nitration waste water, i.e. water containing di- and tri-nitrophenols, and cresol contaminated nitration waste water, i.e. water containing di- and tri-nitrophenols as well as di- and tri-nitrocresols.

EXAMPLE 1 - NON-CRESOL CONTAMINATED WATER

The non-cresol contaminated water utilized was nitration waste water resulting from the production of mononitrobenzene through the adiabatic nitration of benzene with nitric acid in the presence of sulfuric acid. The nitration waste water utilized was not contaminated with cresol compounds. The mononitrobenzene was essentially removed from the nitration waste water by toluene extraction at a high pH, i.e. approximately from about 12-14 (which is the normal feed pH), prior to subjecting the water to pH adjustment and precipitation. The toluene extraction utilized to remove the mononitrobenzene from the solution was a conventional solvent extraction and did not involve any pH adjustment of the waste water. A 5:1 water/toluene ratio was employed. The mononitrobenzene concentration was substantially reduced to a trace amount by the one step extraction leaving a nitration waste water with a 1:2 ratio of 2,4-DNP to picric acid.

Fifty gallons of the non-cresol contaminated nitration waste water as above obtained was pH adjusted from an initial pH of 9.54 to a pH of 2.5 through the addition of sulfuric acid to the waste water. The pH was monitored with a pH sensor while the sulfuric acid was added with agitation until the desired pH was reached. Approximately 600 ml of plant strength (approximately 72%) sulfuric acid was required to adjust the solution pH from 9.54 to 2.5. Once the desired pH level was obtained, the pH was allowed to stabilize. As the acid was added to the solution, a color change from dark maroon to light rust or orange occurred at a pH of about 4.08 to 4.2. Suspended crystals were observed in the solution at these pH levels and below in the acidification process. The sulfuric acid was added incrementally over a period of approximately two hours to allow for the dispersion of the evolved heat and the nitric oxide vapors ($NO_x$) formed. It is noted that a substantial amount of $NO_x$ is generated during the acidification process. The generation of $NO_x$ is the result of salts of $NO_x$ being acidified and is not believed to be due to the destruction of any of the nitrophenols present. The solution temperature was controlled between 30° C. and 35° C.

The pH adjusted solution was then vacuum filtered using a stainless steel tank to hold the mother liquor. The bulk of the crystals formed following the pH adjustment were in the bottom of the reaction vessel. 527 grams of 2,4-DNP crystals were obtained. The recovered crystals were subjected to washing with water to remove any picric acid entrapped in the filtered crystals. The amount of 2,4-DNP removed from the total amount of 2,4-DNP was estimated to be 60% by liquid chromatography analysis of the mother liquor.

The liquid chromatography analysis was performed using a 40% methanol/60% 4.5 pH water solvent system. The flow rate through the column was 1 ml/min. Detection was performed at 254 nm. An Alltech 5-micron, Econosphere C-18 column, 25 cm×4.6 mm was utilized in the liquid chromatography system. Injections were in microliters. The data reduction was performed utilizing a Spectraphysics Model 4270 integrator.

Several representative samples of the crystals were analyzed using the liquid chromatography techniques. Multiple injections verified a fairly consistent analysis and results. The crystal sample recovered consisted of 99.20% 2,4-DNP, 0.70% 2,6-dinitrophenol, 0.04% picric acid, and 0.05% mononitrobenzene.

EXAMPLE 2 - CRESOL CONTAMINATED WATER

The cresol contaminated water utilized was nitration waste water resulting from the production of mononitrobenzene as set forth above in Example 1. Also, as in Example 1, the mononitrobenzene was essentially extracted from the waste water prior to pH adjustment and precipitation.

The cresol contaminated water contained a 3:1 content ratio of 2,4-DNP to picric acid. The procedure utilized with the cresol contaminated water was the same as utilized with the non-cresol contaminated water in Example 1. However, when the solution pH of the waste water was adjusted to a value of 2.7, a cresol content of 3.97% was present in the 2,4-DNP crystals obtained. A maximum purity, i.e., approximately less than 1% cresol content, was obtained when the pH value of the solution was adjusted to 2.5. The 2,4-DNP crystals obtained at a pH of 2.5 contained only 1.2% 2,6-dinitro-para-cresols, 0.7% 2,6-dinitrophenol, and only a trace of 4,6-dinitro-ortho-cresol.

When the pH values of the solution were lowered below 2.5, the relative purity of the 2,4-DNP crystals was decreased due to the precipitation of picric acid. Picric acid was selectively recovered from the nitration waste water in a substantially pure form at a pH in the range of from about 0.5 to 0.7.

EXAMPLE 3 - NON-CRESOL CONTAMINATED WATER

This example compares the recovery of 2,4-DNP when extraction of mononitrobenzene (MNB) is performed prior to subjecting the waste water to the process of the invention with the recovery of 2,4-DNP where no prior extraction of MNB is performed. As seen from the data, extraction of MNB does not substantially affect the purity of the 2,4-DNP recovered since the majority of the MNB remains in the waste water stream feed. It is also clear, however, that prior extraction of MNB is preferred since the 2,4-DNP recovered where a prior extraction occurred has a higher purity level due to the reduced presence of MNB.

| (A) 2,4-DNP Recovery Without Prior Extraction of MNB | | | | |
|---|---|---|---|---|
| STREAM | 1 | 2 | 3 | 4 |
| 2,4 DNP | 49.9 | 0.0 | 44.9 | 5.0 |
| 2,6 DNP | 3.6 | 0.0 | 1.8 | 1.8 |
| Picric Acid | 89.1 | 0.0 | 0.0 | 89.1 |
| MNB | 17.8 | 0.0 | 4.5 | 13.4 |
| NaOH | Varies | 0.0 | 0.0 | 0.0 |
| NaSO$_4$ | Varies | 0.0 | Unknown | Varies |
| H$_2$SO$_4$ | 0.0 | 91.8 | 0.0 | 91.8 |
| Water | 11,737.4 | 2.9 | 7.7 | 11,732.6 |
| lb/h | 11,897.8 | 94.7 | 58.9 | 11,933.6 |
| GPM | 22.0 | 0.1 | | 22.1 |
| pH | 9-12 | | | 2.0 |

| (B) 2,4-DNP Recovery Following Extraction Of MNB From Waste Water | | | | |
|---|---|---|---|---|
| STREAM | 1 | 2 | 3 | 4 |
| 2,4 DNP | 49.9 | 0.0 | 44.9 | 5.0 |
| 2,6 DNP | 3.6 | 0.0 | 1.8 | 1.8 |
| Picric Acid | 89.1 | 0.0 | 0.0 | 89.1 |
| MNB | 0.5 | 0.0 | 0.1 | 0.4 |
| NaOH | Varies | 0.0 | 0.0 | 0.0 |
| NaSO$_4$ | Varies | 0.0 | Unknown | Varies |
| H$_2$SO$_4$ | 0.0 | 91.8 | 0.0 | 91.8 |
| Water | 11,737.4 | 2.9 | 7.7 | 11,732.6 |
| lb/h | 11,880.5 | 94.7 | 54.5 | 11,920.7 |
| GPM | 22.0 | 0.1 | | 22.1 |
| pH | 9-12 | | | 2.0 |

1 - Waste water feed
2 - Sulfuric acid feed
3 - Recovered 2,4-DNP product feed following acidification, precipitation and filtration of waste water feed
4 - Waste water feed following recovery of 2,4-DNP
GPM—gallons per minute Accordingly, 2,4-DNP and picric acid can be selectively recovered in a substantially pure form by controlling the solution pH of nitration waste water regardless of the presence or absence of cresols.

As will be apparent to one skilled in the art, various modifications can be made within the scope of the aforesaid description. Such modifications being within the ability of one skilled in the art form a part of the present invention and are embraced by the appended claims.

It is claimed:

1. A process for selectively recovering a nitrophenolic by-product from nitration waste water by precipitation, said nitrophenolic by-product being 2,4-dinitrophenol, comprising controlling the pH of said nitration waste water within the pH range of from about 4.0 to 2.0 through the addition of sulfuric acid to said nitration waste water, thereby influencing the solubility of said 2,4-dinitrophenol causing said 2,4-dinitrophenol to crystalize out of said nitration waste water in substantially pure form.

2. A process for selectively recovering a nitrophenolic by-product from nitration waste water by precipitation, said nitrophenolic by-product being picric acid, comprising controlling the pH of said nitration waste water within the pH range of from about 0.5 to 0.7 through the addition of sulfuric acid to said nitration waste water, thereby influencing the solubility of said picric acid causing said picric acid to crystallize out of said nitration waste water in substantially pure form.

3. A process for selectively recovering a nitrophenolic by-product in substantially pure form from nitration waste water, said nitrophenolic by-product being 2,4-dinitrophenol, comprising:
   (1) adding sulfuric acid to said nitration waste water in an amount sufficient to adjust the solution pH of said nitration waste water to a pH within the range of from about 4.0 to 2.0 thereby forming crystals of said 2,4-dinitrophenol;
   (2) allowing said crystals formed in the pH adjusted nitration waste water of step (1) to settle; and
   (3) separating said crystals from said water of step (2).

4. A process for selectively recovering a nitrophenolic by-product in substantially pure form from nitration waste water, said nitrophenolic by-product being picric acid, comprising:
   (1) adding sulfuric acid to nitration waste water in an amount sufficient to adjust the solution pH of said nitration waste water to a pH within the range of from about 0.7 to 0.5 thereby forming crystals of said picric acid;
   (2) allowing said crystals formed in the pH adjusted nitration waste water of step (1) to settle; and
   (3) separating said crystals from said water of step (2).

5. A process for selectively recovering a nitrophenolic by-product from nitration waste water by precipitation, said nitrophenolic by-product being a member of the group consisting of 2,4-dinitrophenol and picric acid comprising controlling the pH of said nitration waste water within the pH range of from about 4.0 to 0.5 through the addition of sulfuric acid to said nitration waste water to influence the solubility of said nitrophenolic by-product causing said nitrophenolic by-product to crystalize out of said nitration waste water, wherein said controlling of the pH is carried out in such a manner that said 2,4-dinitrophenol is recovered first in substantially pure form followed by recovering said picric acid in substantially pure form.

6. A process according to claim 1 including the step of washing said crystals obtained in step (3).

* * * * *